United States Patent [19]

Treiber et al.

[11] 4,336,263

[45] Jun. 22, 1982

[54] 1,4-CYCLOALKANO-OXAZEPINES, SALTS THEREOF AND ANALGESIC USES THEREOF

[75] Inventors: Hans J. Treiber, Bruehl; Dieter Lenke, Ludwigshafen; Wolfgang Worstmann, Gruenstadt, all of Fed. Rep. of Germany

[73] Assignee: BASF Aktiengesellschaft, Fed. Rep. of Germany

[21] Appl. No.: 193,947

[22] PCT Filed: Oct. 22, 1979

[86] PCT No.: PCT/EP79/00080

§ 371 Date: Jun. 26, 1980

§ 102(e) Date: Jun. 16, 1980

[87] PCT Pub. No.: WO80/00838

PCT Pub. Date: May 1, 1980

[30] Foreign Application Priority Data

Oct. 26, 1978 [DE] Fed. Rep. of Germany ....... 2846567

[51] Int. Cl.³ ................. C07D 267/14; C07D 267/12; A61K 31/395
[52] U.S. Cl. ................................. 424/244; 260/330.8
[58] Field of Search ........................................ 260/333

[56] References Cited

U.S. PATENT DOCUMENTS 3,598,808 8/1971 Szmuszkovicz ..................... 260/333
3,830,803 8/1974 Klohs et al. ......................... 260/333

FOREIGN PATENT DOCUMENTS 1620198 9/1974 Fed. Rep. of Germany .
2609601 9/1976 Fed. Rep. of Germany .

Primary Examiner—Norma S. Milestone
Attorney, Agent, or Firm—Keil & Witherspoon

[57] ABSTRACT

The invention relates to novel 1,4-cycloalkano-oxazepines of the general formula

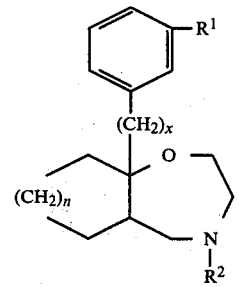

where $R^1$ is hydrogen, hydroxyl or alkoxy or acyloxy of 1 to 4 carbon atoms, $R^2$ is a hydrocarbon radical of 1 to 3 carbon atoms, n is 1, 2 or 3 and x is 0 or 1, and of its salts with physiologically acceptable acids; processes for their preparation, and their use in therapy.

The novel substances are suitable for the pharmacotherapy of pains of various origins.

11 Claims, No Drawings

1,4-CYCLOALKANO-OXAZEPINES, SALTS THEREOF AND ANALGESIC USES THEREOF

TECHNICAL FIELD

The invention relates to novel 1,4-cycloalkano-oxazepines, processes for their preparation and their use in combating pain (algias).

PRIOR ART

German Pat. No. 1,620,198 discloses that certain benzoxazocines have an analgesic action. The best-known of these compounds is Nefopam (5-methyl-1-phenyl-3,4,5,6-tetrahydro-1H-benz[f]-2,5-oxazocine).

DESCRIPTION OF INVENTION

We have found compounds which are substantially more active than Nefopam.

The present invention relates to 1,4-cycloalkano-oxazepines of the general formula I

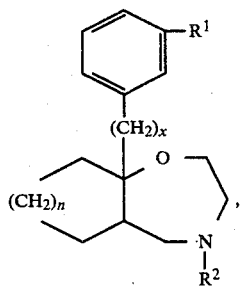

where $R^1$ is hydrogen, hydroxyl or alkoxy or acyloxy of 1 to 4 carbon atoms, $R^2$ is a hydrocarbon radical of 1 to 3 carbon atoms, n is 1, 2 or 3 and x is 0 or 1, and of their salts with physiologically acceptable acids. The invention also relates to a process for the preparation of the 1,4-cycloalkano-oxazepines of the general formula I, wherein a compound of the general formula II

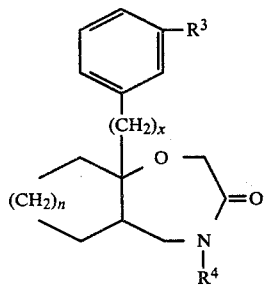

where $R^3$ is hydrogen or alkoxy of 1 to 4 carbon atoms and $R^4$ is a hydrocarbon radical of 1 to 3 carbon atoms or is benzyl, is reduced, after which, where appropriate, alkoxy is replaced by hydroxyl or acyloxy and/or benzyl is replaced by a hydrocarbon radical and, if desired, the resulting compound is converted to a salt with a physiologically acceptable acid.

Finally, the invention also relates to pharmaceuticals containing 1,4-cycloalkano-oxazepines of the general formula I and to the use of the novel substances in combating pain (algias).

The compounds I contain two asymmetric carbon atoms, so that they can in principle form two diastereomeric series. The present invention only relates to those compounds in which the two rings are cis-linked to one another. The novel compounds can be prepared in the form of their racemates and in the form of their antipodes.

A strong reducing agent, eg. diborane or, preferably, lithium aluminum hydride, is required for reducing a compound II. Particularly suitable solvents are tetrahydrofuran, dimethoxyethane, dioxane and ether.

The reduction takes place at an elevated temperature, preferably at the boiling point of the solvent.

A benzyl radical in the 4-position can easily be removed by catalytic hydrogenation. The hydrogenation may be carried out in an alcohol, eg. methanol or ethanol, or in acetic acid as the solvent, preferably at room temperature, and using a noble metal of main group 8 of the periodic table, preferably Pd/charcoal, as the catalyst.

The resulting secondary amine can be alkylated by means of an alkyl halide in the presence of an acid acceptor, such as an alkali metal carbonate, alkali metal hydroxide or tertiary amine, in a solvent such as methyl isobutyl ketone, at about 0°–150° C., preferably at about 80° C. The alkylation can also be effected by reaction with a carboxylic acid followed by reduction of the C=O group with lithium aluminum hydride.

The replacement of methoxy by hydroxyl may be carried out with, for example, sodium methylmercaptide, in a dipolar aprotic solvent, eg. hexamethylphosphorotriamide, dimethylsulfoxide or dimethylformamide, at 50°–200° C., preferably 80°–150° C.

Virtually all conventional methods may be employed for acylating the free hydroxyl groups. The simplest method is to react such groups with an acid anhydride or acid halide at an elevated temperature.

The starting materials of the general formula II, required for the preparation of the novel compounds, have not previously been described. They may be prepared as follows:

A Mannich compound of the formula III is prepared from a cycloalkanone, formaldehyde and a secondary benzylamine derivative (cf. Organic Reactions I (1942), British Pat. No. 615,136, J. Chem. Soc. 1950, 1512 and J. Org. Chem. 24, (1959), 1069):

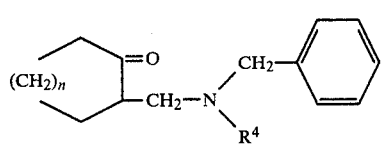

Reaction of III with an appropriate Grignard compound gives the compound IV (cf. J. Am. Chem. Soc. 71 (1949), 2050, British Pat. No. 997,399, German Pat. No. 1,199,764 and Arzneim. Forsch. 28 (1978), 107):

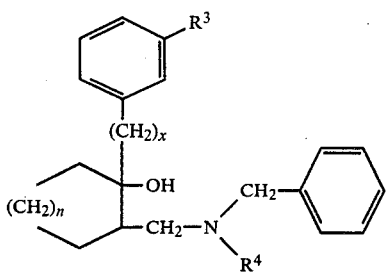

IV from which the benzyl radical is removed by hydrogenation. Reaction of the resulting compound with chloroacetyl chloride in the presence of dilute sodium hydroxide solution or triethylamine gives the compound V

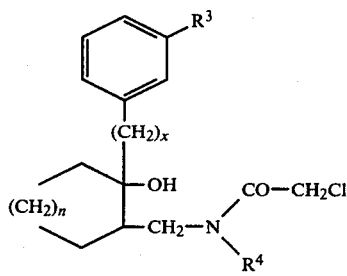

V

The compound II may then be prepared from V by heating with a base, eg. potassium tert.-butanolate, in dimethylsulfoxide.

In compound V, the free OH group and the $CH_2$—$NR^4$—CO—$CH_2Cl$ group are in the cis-position relative to one another, if the compound is prepared by the above method.

If it is desired to prepare compound I in the form of its optical antipodes, it is advantageous to separate the racemates at the stage of compound IV.

The compounds according to the invention exhibit a pronounced analgesic action.

The model used for testing the analgesic action was the tail flick test of D'AMOUR and SMITH (J. Pharmacol. 72 (1941), 74–79). In this experiment, the compounds to be tested were administered intraperitoneally or orally, as aqueous solutions (injection volume 10 ml/kg) to groups of 10 female mice (NMRI strain) weighing 20–22 g each.

Pain reactions are caused before, and 30 minutes after, the administration of the compound, by means of thermal irritation (the tail being exposed to focused heat radiation from a halogen lamp for at most 30 seconds).

The time until the tail is drawn out of the radiation zone by reflex action is measured, and taken as the reaction time. Its average value, for 670 untreated animals, is 6.5±0.29 sec.

Analgesic substances increase the reaction time, to an extent depending on the dose. There is a linear relationship between the logarithms of the doses (mg/kg) and of the relative increase in reaction time (Δ%), from which the dose, defined as the ED 100%, which doubles the reaction time can be calculated by means of regression analysis. For a radiation exposure period of at most 30 seconds, the maximum possible increase in the reaction time is about 360%.

A dose-dependent analgesic action is demonstrable both after intraperitoneal and after oral administration (Table 1). The novel substances are, in this test, substantially superior to the known analgesic Nefopam (5-methyl-1-phenyl-3,4,5,6-tetrahydro-1H-2,5-benzoxazocine), particularly using oral administration, namely the pharmacotherapeutically important route of administration. The activity of the compounds according to the invention is from about 2 to 5 times greater. The greater oral activity is accompanied by an increase in the relative enteral activity, this being a parameter of exceptional importance with regard to safety of use. The enteral activity is expressed as the quotient of the effective doses (ED 100%) for intraperitoneal and oral administration. It is from 0.35 to 0.96 for the novel compounds and is thus from 2.1 to 5.6 times greater than the enteral activity of Nefopam.

Under the conditions of the tail flick test, the reaction time can be increased by the compounds according to the invention, using either route of administration, the maximum increase without causing fatalities due to toxic effects of the compounds being 275–416% for intraperitoneal administration and 280–297% for oral administration. In contrast, with Nefopam the maximum possible increases are only 192% (21.5 mg/kg administered intraperitoneally) and 93% (46.4 mg/kg administered orally). Higher doses (46.4 mg/kg administered intraperitoneally or 100 mg/kg administered orally) already prove lethal and kill 60% of the treated animals (Table 1).

The comparatively low toxicity of the novel compounds can also be deduced from the acute lethal dose (LD 50) for intraperitoneal administration (Table 2). The LD 50 values are from about 90% to 240% higher than those of Nefopam.

TABLE 1

| Compound from Example No. | Intraperitoneal administration | | | | Oral administration | | | | |
|---|---|---|---|---|---|---|---|---|---|
| | ED 100%[1] | relative activity | Maximum action[2] | | ED 100% | relative activity | Maximum action[2] | | Q[3] |
| | | | mg/kg | Δ% | | | mg/kg | Δ% | |
| 3 | 11.4 | 0.71 | 46.4 | 416 | 17.0 | 2.73 | 100 | 397 | 0.67 |
| 6 | 4.66 | 1.73 | 46.4 | 380 | 9.49 | 4.89 | 46.4 | 364 | 0.49 |
| 7 | 6.55 | 1.23 | 46.4 | 364 | 18.6 | 2.50 | 46.4 | 332 | 0.35 |
| 9 (−) | 11.0 | 0.74 | 46.4 | 348 | 17.6 | 2.64 | 100 | 397 | 0.63 |
| 9 (+) | 16.7 | 0.48 | 46.4 | 249 | 23.5 | 1.97 | 100 | 370 | 0.71 |
| 7 β | 12.6 | 0.64 | 46.4 | 275 | 13.1 | 3.54 | 100 | 280 | 0.96 |

TABLE 1-continued

| Compound from Example No. | Intraperitoneal administration | | | | Oral administration | | | | |
|---|---|---|---|---|---|---|---|---|---|
| | ED 100%[1] | relative activity | Maximum action[2] | | ED 100% | relative activity | Maximum action[2] | | Q[3] |
| | | | mg/kg | Δ% | | | mg/kg | Δ% | |
| Nefopam | 8.08 | ≡1.00 | 21.5[4] | 192 | 46.4 | 1.00 | 46.4[5] | 93 | 0.17 |

[1] Dose in mg/kg which increases the reaction time by 100%

[2] Maximum increase in reaction time for a dosage step of $\sqrt[3]{10}$

[3] $Q = \text{enteral activity} = \frac{\text{ED 100\% for intraperitoneal administration}}{\text{ED 100\% for oral administration}}$

[4] 6 out of 10 animals died at 46.4 mg/kg

[5] 6 out of 10 animals died at 100 mg/kg

TABLE 2

| Compound of Example No. | LD 50 mg/kg | Relative toxicity |
|---|---|---|
| 3 | 110 | 0.52 |
| 6 | 127 | 0.45 |
| 7 | 165 | 0.35 |
| 9 (−) | 145 | 0.40 |
| 9 (+) | 110 | 0.52 |
| 7 β | 194 | 0.30 |
| Nefopam | 57.3 | ≡ 1.00 |

COMMERCIAL UTILITY

The novel compounds are suitable for the pharmacotherapy of pains of various origins. They may be administered orally or parenterally (intravenously or intramuscularly) in the conventional manner.

The dosage depends on the age, condition and weight of the patient and on the route of administration. As a rule, the daily dose of active compound is from about 0.1 to 2.0 mg/kg of body weight for oral administration and from about 0.05 to 1.0 mg/kg of body weight for parenteral administration. In a normal case, satisfactory results are achieved with a daily dose of from 0.3 to 1.5 mg/kg administered orally or from 0.1 to 0.5 mg/kg administered parenterally.

The novel compounds may be used in one of the solid or liquid conventional galenical forms for administration, for example as tablets, capsules, powders, granules, dragees, solutions or suppositories. These are prepared in the conventional manner by formulating the active compound together with the conventional galenical auxiliaries, such as tablet binders, fillers, preservatives, tablet-disintegrating agents, flow regulators, plasticizers, wetting agents, dispersants, emulsifiers, solvents, retarders and/or antioxidants (cf. L. G. Goodman and A. Gilman: The Pharmacological Basis of Therapeutics).

The novel compounds can also be administered in the form of their salts with physiologically acceptable acids. Examples of such acids are hydrochloric acid, sulfuric acid, phosphoric acid, tartaric acid, citric acid, fumaric acid, acetic acid, formic acid, succinic acid, maleic acid, lactic acid and amidosulfonic acid.

PREPARATION OF THE STARTING MATERIALS (a) 2-(N-Benzylmethylamino)-methyl-cyclopentanone hydrochloride 87.5 g (0.55 mole) of N-benzylmethylamine hydrochloride, 84 g (1.0 mole) of cyclopentanone, 45 g of paraformaldehyde ( $\triangleq$1.5 moles of formaldehyde) and 500 ml of ethanol are refluxed for one hour whilst stirring, during which solution occurs. After the solution has cooled, the solvent is distilled off under reduced pressure, the oily residue is dissolved in 100 ml of isopropanol and 500 ml of ethyl acetate are then added, whereupon the product crystallizes out after some time.

Yield 75 g (54% of theory). Melting point 129°–130° C.

The following compounds were obtained in a similar manner:

| n | R | Melting point of the hydrochloride (°C.) | Yield |
|---|---|---|---|
| 2 | CH₃ | 140 | 83% |
| 2 | CH₂—⌬ | 250–251 | 48% |
| 3 | CH₃ | 120–123 | 43% |

(b) 2-(N-Benzylmethylamino)-methyl-1-(3-methoxybenzyl)cyclohexanol 67 g (0.25 mole) of 2-(N-benzylmethylamino)methyl-cyclohexanone hydrochloride obtained as described in (a) are introduced in the course of 30 minutes, whilst stirring and cooling, into a Grignard solution which has been prepared from 110 g (0.7 mole) of 3-methoxybenzyl chloride, 16.8 g of magnesium and 700 ml of dry ether; stirring is continued for 16 hours at room temperature, the reaction mixture is decomposed with an excess of concentrated ammonium chloride solution, the ether layer is separated off and dried with sodium sulfate, the ether is driven off and the residue is distilled under reduced pressure.

Yield: 60 g (68% of theory). Melting point 200°–205° C./0.007 mbar.

The following compounds were prepared in a similar manner:

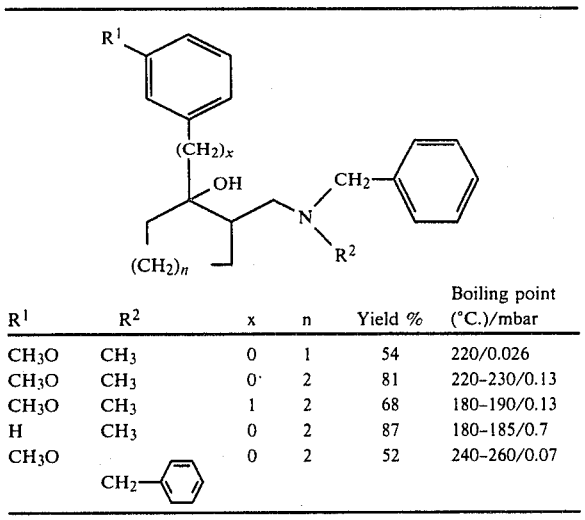

| R¹ | R² | x | n | Yield % | Boiling point (°C.)/mbar |
|---|---|---|---|---|---|
| CH₃O | CH₃ | 0 | 1 | 54 | 220/0.026 |
| CH₃O | CH₃ | 0 | 2 | 81 | 220–230/0.13 |
| CH₃O | CH₃ | 1 | 2 | 68 | 180–190/0.13 |
| H | CH₃ | 0 | 2 | 87 | 180–185/0.7 |
| CH₃O | CH₂–C₆H₅ | 0 | 2 | 52 | 240–260/0.07 |

Resolution of the racemate of 2-(N-benzylmethylamino)methyl-1-(3-methoxy-phenyl)-cyclohexanol A solution of 150 g (0.44 mole) of 2-(N-benzylmethylamino)-methyl-1-(3-methoxy-phenyl)-cyclohexanol and 168 g (0.44 mole) of L(−)-O,O-dibenzoyltartaric acid monohydrate in 1,000 ml of isopropanol is prepared; from this, the dibenzoyltartrate of the levo-rotatory base crystallizes out. After recrystallizing this material twice from a 3-fold amount of isopropanol, 130 g (86% of theory) of a product is obtained which shows no change in optical rotation after further recrystallizations.

Specific optical rotation: $[\alpha]_D^{20} = -77°$ (methanol, C=27 mg/ml).

The salt is converted in the conventional manner to the base, having the following specific optical rotation: $[\alpha]_D^{20} = -89°$ (methanol, C=22 mg/ml).

If D(+)-O,O-dibenzoyltartaric acid is used for the resolution, the dibenzoyltartrate of the dextrorotatory base, having a specific optical rotation $[\alpha]_D^{20} = +77°$, and the base, having a specific optical rotation $[\alpha]_D^{20} = +89°$, are obtained similarly.

(c)
2-(Benzylamino)-methyl-1-(3-methoxyphenyl)-cyclohexanol 43.0 g (0.103 mole) of 2-dibenzylaminomethyl-1-(3-methoxy-phenyl)-cyclohexanol (prepared as described in (b)) are dissolved in 300 ml of methanol and hydrogenated under atmospheric pressure at room temperature in the presence of 10 g of a 5% strength palladium/charcoal catalyst. When one equivalent of hydrogen has been absorbed, the hydrogenation stops. The catalyst is filtered off, the solution is concentrated and the product is distilled under reduced pressure.

Yield: 25 g (73% of theory). Boiling point 180°–190° C./0.07 mbar.

The following compounds were obtained similarly:

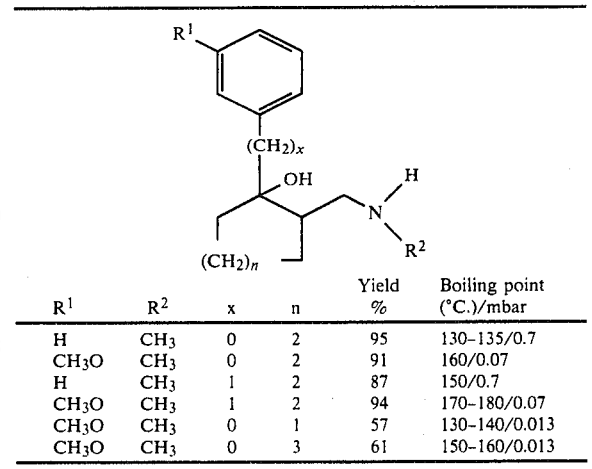

| R¹ | R² | x | n | Yield % | Boiling point (°C.)/mbar |
|---|---|---|---|---|---|
| H | CH₃ | 0 | 2 | 95 | 130–135/0.7 |
| CH₃O | CH₃ | 0 | 2 | 91 | 160/0.07 |
| H | CH₃ | 1 | 2 | 87 | 150/0.7 |
| CH₃O | CH₃ | 1 | 2 | 94 | 170–180/0.07 |
| CH₃O | CH₃ | 0 | 1 | 57 | 130–140/0.013 |
| CH₃O | CH₃ | 0 | 3 | 61 | 150–160/0.013 |

(d)
2-(N-Chloroacetyl)-methylaminomethyl-1-(3-methoxyphenyl)-cyclohexanol 100 ml of 2 N sodium hydroxide solution are added to a solution of 30 g (0.12 mole) of 2-methylaminomethyl-1-(3-methoxyphenyl)-cyclohexanol (cf. (c)) in 300 ml of ether and 17 g (0.15 mole) of chloroacetyl chloride are then added dropwise in the course of 15 minutes, whilst stirring. Thereafter the mixture is heated for 30 minutes and then cooled, the ether layer is separated off and dried with sodium sulfate, and the solvent is distilled off. The residue is used further in its crude form.

Yield: about 100% of theory.

The following compounds were obtained similarly:

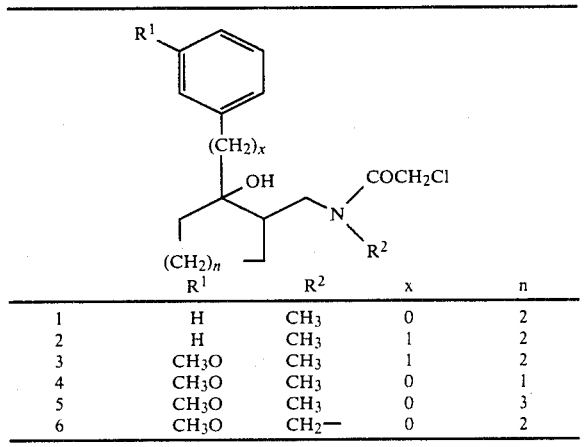

| | R¹ | R² | x | n |
|---|---|---|---|---|
| 1 | H | CH₃ | 0 | 2 |
| 2 | H | CH₃ | 1 | 2 |
| 3 | CH₃O | CH₃ | 1 | 2 |
| 4 | CH₃O | CH₃ | 0 | 1 |
| 5 | CH₃O | CH₃ | 0 | 3 |
| 6 | CH₃O | CH₂– | 0 | 2 |

(e)
4-Methyl-9a-(3-methoxyphenyl)-perhydro-1,4-benzoxazepine-3-OH 16 g (0.05 mole) of the 2-(N-chloroacetyl)-methylaminomethyl-1-(3-methoxyphenyl)-cyclohexanol described in (c) are dissolved in 200 ml of dimethylsulfoxide, with stirring, and 10 g of potassium tert.-butanolate are added a little at a time in the course of 30 minutes, whilst cooling slightly to keep the mixture at 20° C. The mixture is then heated at 50° C. for 30 minutes, after which stirring is continued overnight at room temperature. For working up, the dimethylsulfoxide is distilled off under reduced pressure, the residue is taken up in water, the mixture is extracted with methylene chloride and the organic phase is separated off, dried and concentrated by evaporation.

The residue is recrystallized from 2 parts of isopropanol.

Yield: 8.5 g (65% of theory).
Melting point 120°–121° C.
Boiling point 195°–200° C./0.07 mbar.

The compounds shown below were prepared similarly, but none of them was obtainable in a crystalline form.

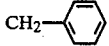

II

| | R¹ | R² | x | n | crude yield |
|---|---|---|---|---|---|
| 1 | H | CH₃ | 0 | 2 | 100 |
| 2 | H | CH₃ | 1 | 2 | 81 |
| 3 | CH₃O | CH₃ | 1 | 2 | 100 |
| 4 | CH₃O | CH₃ | 0 | 1 | 65 |
| 5 | CH₃O | CH₃ | 0 | 3 | 100 |
| 6 | CH₃O | CH₂—⌬ | 0 | 2 | 100 |

Preparation of the End Product

EXAMPLE 1

4-Methyl-9a-(3-methoxybenzyl)-perhydro-1,4-benzoxazepine 40.8 g (0.14 mole) of crude 4-methyl-9a-(3-methoxybenzyl)-perhydro-1,4-benzoxazepine-3-OH (cf. (e) are dissolved in 100 ml of absolute tetrahydrofuran and the solution is slowly added dropwise to a refluxing suspension of 9.5 g (0.25 mole) of lithium aluminum hydride in 250 ml of tetrahydrofuran. The solution is then boiled under nitrogen for 6 hours and cooled, a small amount of water is added, and after distilling off the solvent the crude base is obtained; the latter is then distilled.

The pure base is converted to its hydrochloride by means of a solution of hydrochloric acid in isopropanol.

Yield (base) 24.5 g (60% of theory).
Boiling point 190°–210° C.0.27 mbar.
Hydrochloride: 220°–221° C.

The compounds tabulated below were obtained similarly:

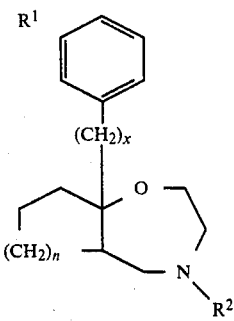

| Example | R¹ | R² | x | n | Yield % | Hydrochloride Melting point, °C. |
|---|---|---|---|---|---|---|
| 2 | H | CH₃ | 0 | 2 | 67 | 250 |
| 3 | CH₃O | CH₃ | 0 | 2 | 74 | 214 |
| 4 | H | CH₃ | 1 | 2 | 58 | 251 |
| 5 | CH₃O | CH₃ | 0 | 3 | 55 | 208–10 |
| 6 | CH₃O | CH₃ | 0 | 1 | 46 | 218–20 |

EXAMPLE 7

(α)

4-Methyl-9a-(3-hydroxyphenyl)-perhydro-1,4-benzoxazepine

A solution of sodium methylmercaptide in ethanol is prepared from 2.3 g (0.1 mole) of sodium, 100 ml of absolute ethanol and 6.2 g (0.1 mole) of ethylmercaptan, the alcohol is then distilled off under reduced pressure, 50 ml of dry dimethylformamide and 5.5 g (0.02 mole) of 4-methyl-9a-(3-methoxyphenyl)-perhydro-1,4-benzoxazepine (obtained as described in Example 1) are added, and the mixture is heated for three hours at 140° C. It is then diluted with 500 ml of water and neutralized with acetic acid, after which the solution is repeatedly extracted with methylene chloride. After combining the methylene chloride extracts and removing the solvent therefrom, the residue is taken up in 100 ml of ether and the product is precipitated as the hydrochloride by introducing hydrogen chloride gas. The hydrochloride is recrystallized from isopropanol.

Yield: 4.6 g (77% of theory).
Melting point 230° C.

(β)

4-Methyl-9a-(3-acetoxyphenyl)-perhydro-1,4-benzoxazepine 3.0 g (0.1 mole) of the compound obtained above and 50 ml of acetic anhydride are refluxed for 3 hours. The excess acetic anhydride is then distilled off under reduced pressure and the residue is recrystallized from a small amount of isopropanol. The compound is obtained as the hydrochloride.

Yield: 2.8 g (82% of theory).
Melting point 210° C.

EXAMPLE 8

(α) 9a-(3-Methoxyphenyl)-perhydro-1,4-benzoxazepine 16 g (0.045 mole) of 4-benzyl-9a-(3-methoxyphenyl)-perhydro-1,4-benzoxazepine (boiling point 240°–260° C./0.07 mbar), prepared by methods similar to that of Example 1, are hydrogenated in the conventional manner with a palladium/charcoal catalyst (5 g of 5% strength Pd on charcoal) in glacial acetic acid; after filtration and distillation, 8.8 g (75% of theory) of 9a-(3-methoxyphenyl)-perhydro-1,4-benzoxazepine, of boiling point 180°–185° C./0.07 mbar, are obtained.

(β)

4-Allyl-9a-(3-methoxyphenyl)-perhydro-1,4-benzoxazepine

The compound obtained above is mixed with 80 ml of methyl isobutyl ketone, 3.2 g of allyl bromide and 3.6 g of potassium carbonate powder and the mixture is refluxed for 6 hours whilst stirring. 100 ml of water are then added, the organic layer is separated off, the solvent is removed, the residue is taken up in ether and the compound is precipitated as the hydrochloride by introducing gaseous hydrogen chloride.

After recrystallization from isopropanol, 6.4 g (57% of theory) of the hydrochloride, of melting point 225° C., are obtained.

If a similar process is carried out using ethyl bromide, 4-ethyl-9a-(3-methoxyphenyl)-perhydro-1,4-benzoxazepine is obtained.

Yield: 52% of theory.
Melting point 195°–196° C.

EXAMPLE 9

(+)- and (−)-4-Methyl-9a-(3-methoxyphenyl)-perhydro-1,4-benzoxazepine

The two optical antipodes of 4-methyl-9a-(3-methoxyphenyl)-perhydro-1,4-benzoxazepine are prepared from (+)- and (−)-2-(N-benzyl-methylamino)-methyl-1-(3-methoxyphenyl)-cyclohexanol, obtained as described in (b), by employing processes c, d and e and the process of Example 1.

Specific optical rotations (measured in methanol, C=20 mg/ml):
Bases: $[\alpha]_D^{20} = \pm 15°$.
Hydrochlorides: $[\alpha]_D^{20} = \pm 35°$.
Melting points: 190°–191° C.

EXAMPLE 10

Tablets of the following composition are molded on a tableting press in the conventional manner:
20.00 mg of 4-methyl-9a-(3-methoxyphenyl)-perhydro-1,4-benzoxazepine
50.00 mg of corn starch
4.50 mg of gelatin
15.00 mg of lactose
7.50 mg of talc
0.75 mg of Aerosil ® (chemically pure silica in a sub-microscopic state of fine division)
2.25 mg of potato starch (as a 6% strength paste).

EXAMPLE 11

Dragees of the following composition are prepared in the conventional manner:
20.00 mg of 4-methyl-9a-(3-acetoxyphenyl)-perhydro-1,4-benzoxazepine
50.00 mg of core composition
40.00 mg of sugar-coating composition.

The core composition consists of 9 parts of corn starch, 3 parts of lactose and 1 part of Luviskol ® VA 64 (a 60:40 vinylpyrrolidone/vinyl acetate copolymer, cf. Pharm. Ind. 1962, 586). The sugar-coating composition consists of 5 parts of cane sugar, 2 parts of corn starch, 2 parts of calcium carbonate and 1 part of talc. The dragees thus prepared are subsequently provided with a coating which is resistant to gastric juices.

EXAMPLE 12

10 g of 4-methyl-9a-(3-methoxybenzyl)-perhydro-1,4-benzoxazepine hydrochloride are dissolved in 2.0 liters of water and the solution is made isotonic acid sodium chloride and is filled, under sterile conditions, into ampoules of 2 ml capacity.

We claim:
1. A 1,4-Cycloalkano-oxazepine of the general formula I

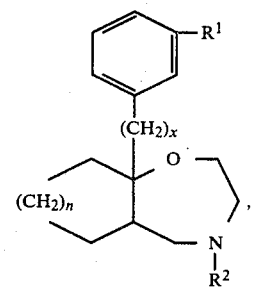

where $R^1$ is hydrogen, hydroxyl or alkoxy or acyloxy of 1 to 4 carbon atoms, $R^2$ is a hydrocarbon radical of 1 to 3 carbon atoms, n is 1, 2 or 3 and x is 0 or 1, or one of its salts with physiologically acceptable acids.

2. A compound selected from the group consisting of 4-methyl-9a-(3-methoxyphenyl)-perhydro-1,4-benzoxazepine, (+)-4-methyl-9a-(3-methoxyphenyl)-perhydro-1,4-benzoxazepine, (−)-4-methyl-9a-(3-methoxyphenyl)-perhydro-1,4-benzoxazepine, 4-methyl-8a-(3-methoxy-phenyl)-perhydro-1,4-cyclopentoxazepine, 4-methyl-9a-(3-hydroxyphenyl)-perhydro-1,4-benzoxazepine and 4-methyl-9a-(3-acetoxyphenyl)-perhydro-1,4-benzoxazepine.

3. A pharmaceutical composition comprising a galenical auxiliary containing an analgesically effective dose of a compound as claimed in claim 2.

4. A pharmaceutical composition comprising a galenical auxiliary containing an analgesically effective dose of a compound as claimed in claim 1.

5. A therapeutic composition comprising a liquid or solid suitable for oral or parenteral administration, said composition containing an analgesically effective amount of a compound as claimed in claim 2.

6. A therapeutic composition comprising a liquid or solid suitable for oral or parenteral administration, said composition containing an analgesically effective amount of a compound as claimed in claim 1.

7. A cycloalkano-oxazepine as claimed in claim 1 wherein the compound is one of said salts.

8. A cycloalkano-oxazepine as claimed in claim 13 wherein said salt is a salt of one of hydrochloric acid, sulfuric acid, phosphoric acid, tartaric acid, citric acid, fumaric acid, acetic acid, formic acid, succinic acid, maleic acid, lactic acid, and amidosulfonic acid.

9. A salt of one of the acids hydrochloric acid, sulfuric acid, phosphoric acid, tartaric acid, citric acid, fumaric acid, acetic acid, formic acid, succinic acid, maleic acid, lactic acid, and amidosulfonic acid and a compound as claimed in claim 2.

10. Process for alleviating pain in patients suffering therefrom, characterized in that an effective quantity of a compound according to claim 1 is administered to the patients.

11. Process for alleviating pain in patients suffering therefrom, characterized in that an effective quantity of a compound according to claim 2 is administered to the patients.

* * * * *